(12) United States Patent
Neelamegam et al.

(10) Patent No.: US 11,771,307 B2
(45) Date of Patent: Oct. 3, 2023

(54) INTERNAL SEAL FOR BIOPSY CAP

(71) Applicant: BOSTON SCIENTIFIC LIMITED, St. Michael (BB)

(72) Inventors: Venkatesh Neelamegam, Tirupur (IN); Shalin Singh Rawat, Rishikesh (IN); Harchetan Singh Aneja, Amritsar (IN); Swami Upadhyay, Raipur (IN); Boopathi Rajarathnam, Salem (IN); Amit Bharos, Jabalpur (IN)

(73) Assignee: BOSTON SCIENTIFIC LIMITED, St. Michael (BM)

( * ) Notice: Subject to any disclaimer, the term of this patent is extended or adjusted under 35 U.S.C. 154(b) by 835 days.

(21) Appl. No.: 16/671,850

(22) Filed: Nov. 1, 2019

(65) Prior Publication Data

US 2020/0138273 A1 May 7, 2020

Related U.S. Application Data

(60) Provisional application No. 62/834,192, filed on Apr. 15, 2019, provisional application No. 62/834,201, (Continued)

(51) Int. Cl.
*A61B 1/00* (2006.01)
*B29D 99/00* (2010.01)
(Continued)

(52) U.S. Cl.
CPC ........ *A61B 1/00137* (2013.01); *A61B 1/0011* (2013.01); *A61B 1/0014* (2013.01);
(Continued)

(58) Field of Classification Search
None
See application file for complete search history.

(56) References Cited

U.S. PATENT DOCUMENTS

| 4,198,959 A | 4/1980 | Otani |
| 5,104,379 A | 4/1992 | Nakamura et al. |

(Continued)

FOREIGN PATENT DOCUMENTS

| AU | 1999027921 A1 | 2/2000 |
| AU | 2001056987 A1 | 2/2000 |

(Continued)

OTHER PUBLICATIONS

Cook Medical—"Fusion® Wire Guide Locking Device" URL: https://www.cookmedical.com/products/esc_fswl_webds/© Cook 2021.
(Continued)

*Primary Examiner* — Timothy J Neal
(74) *Attorney, Agent, or Firm* — Seager, Tufte & Wickhem, LLP

(57) ABSTRACT

Biopsy caps and seals, and methods for making and using the same may be provided in conjunction with an endoscope assembly. A seal may include a main body including a circumferential outer wall surrounding a central lumen. The seal may include at least one support wall extending radially from the outer wall towards a center of the lumen, and at least one helical flap extending from the support wall helically downward along an inner surface of the outer wall, where the at least one helical flap defines an opening at the center of the lumen. The seal may alternatively include a plurality of projections extending radially inward from the outer wall towards a center of the lumen, where the plurality of projections are arranged in a series of circumferentially and angularly offset layers.

20 Claims, 17 Drawing Sheets

Related U.S. Application Data filed on Apr. 15, 2019, provisional application No. 62/768,808, filed on Nov. 16, 2018, provisional application No. 62/755,024, filed on Nov. 2, 2018.

(51) Int. Cl.
| | | |
|---|---|---|
| *A61B 1/015* | (2006.01) | |
| *A61B 1/018* | (2006.01) | |
| *A61B 10/02* | (2006.01) | |
| *A61B 10/04* | (2006.01) | |

(52) U.S. Cl.
CPC ...... *A61B 1/00064* (2013.01); *A61B 1/00147* (2013.01); *A61B 1/015* (2013.01); *A61B 1/018* (2013.01); *A61B 10/0275* (2013.01); *A61B 10/04* (2013.01); *B29D 99/0053* (2013.01)

(56) References Cited

U.S. PATENT DOCUMENTS

| | | | |
|---|---|---|---|
| 5,312,363 A | | 5/1994 | Ryan et al. |
| 5,743,884 A | * | 4/1998 | Hasson .............. A61B 17/3462 |
| | | | 604/249 |
| 6,605,075 B1 | | 8/2003 | Burdulis |
| 7,226,411 B2 | | 6/2007 | Akiba |
| 7,473,221 B2 | | 1/2009 | Ewers et al. |
| 7,637,863 B2 | | 12/2009 | Deal et al. |
| 7,670,285 B2 | | 3/2010 | Yamaya |
| 7,670,316 B2 | | 3/2010 | Windheuser et al. |
| 7,803,107 B2 | | 9/2010 | Carrillo |
| 7,967,744 B2 | | 6/2011 | Kaye et al. |
| 8,012,129 B2 | | 9/2011 | Bettuchi et al. |
| 8,152,774 B2 | | 4/2012 | Pasqualucci |
| 8,231,525 B2 | | 7/2012 | Cohen et al. |
| 8,333,693 B2 | | 12/2012 | Hamazaki |
| 8,343,041 B2 | | 1/2013 | Byers et al. |
| 8,480,570 B2 | | 7/2013 | Tinkham et al. |
| 8,702,596 B2 | | 4/2014 | Kaye et al. |
| 8,753,264 B2 | | 6/2014 | Carrillo, Jr. et al. |
| 8,974,377 B2 | | 3/2015 | Yamane |
| 9,089,261 B2 | | 7/2015 | Greenburg et al. |
| 9,101,738 B2 | | 8/2015 | Eden |
| 9,149,173 B2 | | 10/2015 | Scopton et al. |
| 9,622,776 B2 | | 4/2017 | Oberlaender et al. |
| 9,955,998 B2 | | 5/2018 | Kleyman |
| 9,986,895 B2 | | 6/2018 | Meloul |
| 2005/0171402 A1 | | 8/2005 | Cohen et al. |
| 2006/0195117 A1 | | 8/2006 | Rucker et al. |
| 2007/0238928 A1 | | 10/2007 | Maseda et al. |
| 2007/0244356 A1 | | 10/2007 | Carrillo et al. |
| 2007/0282166 A1 | | 12/2007 | Ayala et al. |
| 2007/0293719 A1 | | 12/2007 | Scopton et al. |
| 2009/0005799 A1 | | 1/2009 | Franer et al. |
| 2009/0088600 A1 | | 4/2009 | Meloul |
| 2009/0287052 A1 | | 11/2009 | Amos et al. |
| 2010/0081878 A1 | | 4/2010 | Byers et al. |
| 2010/0087705 A1 | * | 4/2010 | Byers .................. A61M 39/06 |
| | | | 600/104 |
| 2010/0240956 A1 | | 9/2010 | Secrest et al. |
| 2012/0004507 A1 | | 1/2012 | Kaye |
| 2012/0071713 A1 | | 3/2012 | Kaye et al. |
| 2012/0253128 A1 | | 10/2012 | Yamane |
| 2013/0150793 A1 | | 6/2013 | Beissel et al. |
| 2013/0304116 A1 | | 11/2013 | Yamane |
| 2015/0190170 A1 | | 7/2015 | Frederick et al. |
| 2016/0206859 A1 | | 7/2016 | Eden |
| 2017/0202438 A1 | | 7/2017 | Ogi |
| 2017/0319828 A1 | | 11/2017 | Doepker et al. |
| 2018/0310806 A1 | | 11/2018 | Gavalis et al. |
| 2019/0046016 A1 | | 2/2019 | Rajarathnam et al. |
| 2019/0142463 A1 | | 5/2019 | Zhu |
| 2020/0138272 A1 | | 5/2020 | Neelamegam et al. |
| 2020/0138274 A1 | | 5/2020 | Aneja et al. |
| 2020/0138276 A1 | | 5/2020 | Aneja et al. |
| 2020/0138277 A1 | | 5/2020 | Neelamegam et al. |
| 2020/0138419 A1 | | 5/2020 | Aneja et al. |

FOREIGN PATENT DOCUMENTS

| | | |
|---|---|---|
| CN | 105816208 A | 8/2016 |
| CN | 205697867 U | 11/2016 |
| EP | 1997444 A2 | 12/2008 |
| EP | 1406691 B1 | 1/2010 |
| EP | 2505119 A1 | 10/2012 |
| EP | 2564758 A1 | 3/2013 |
| EP | 2574271 A1 | 4/2013 |
| EP | 2574271 B1 | 11/2014 |
| JP | S6129703 A | 2/1986 |
| JP | H11-253396 A | 9/1999 |
| JP | 2001104315 A | 4/2001 |
| JP | 2003-533297 A | 11/2003 |
| JP | 2005080867 A | 3/2005 |
| JP | 2008123063 A | 5/2008 |
| JP | 2008529723 A | 8/2008 |
| JP | 2009268777 A | 11/2009 |
| WO | 0187398 A2 | 11/2001 |
| WO | 2005011791 A2 | 2/2005 |
| WO | 2008101286 A1 | 8/2008 |
| WO | 2009143129 A1 | 11/2009 |
| WO | 2009143137 A1 | 11/2009 |
| WO | 2018024109 A1 | 2/2018 |

OTHER PUBLICATIONS

International Search Report and Written Opinion for application No. PCT/IB2019/059411, dated Jun. 25, 2020, 14 pages.

International Search Report and Written Opinion for the International Patent Application No. PCT/IB2019/059413, dated Feb. 17, 2020, 10 pages.

International Search Report and Written Opinion for the International Patent Application No. PCT/IB2019/059404, dated Feb. 17, 2020, 10 pages.

International Search Report and Written Opinion for the International Patent Application No. PCT/IB2019/059407, dated Feb. 14, 2020, 11 pages.

International Search Report and Written Opinion for the International Patent Application No. PCT/IB2019/059408, dated Feb. 14, 2020, 12 pages.

International Search Report and Written Opinion for the International Patent Application No. PCT/IB2019/059409, dated Feb. 13, 2020, 11 pages.

* cited by examiner

INTERNAL SEAL FOR BIOPSY CAP

PRIORITY

This application claims the benefit of priority under 35 USC § 119 to U.S. Provisional Patent Application Ser. No. 62/755,024, filed Nov. 2, 2018 and titled "Attachments for Endoscopes," U.S. Provisional Patent Application Ser. No. 62/768,808, filed Nov. 16, 2018 and titled "Internal Seal for Biopsy Cap," U.S. Provisional Patent Application Ser. No. 62/834,192, filed Apr. 15, 2019 and titled "Biopsy Cap and Biopsy Cap Housing," and to U.S. Provisional Patent Application Ser. No. 62/834,201, filed Apr. 15, 2019 and titled "Devices, Systems, and Methods For Providing Sealable Access To A Working Channel," the disclosures of which are incorporated by reference herein in their entirety and for all purposes.

TECHNICAL FIELD

The present disclosure relates generally to the field of medical devices such as endoscopes, guidewires, guide tubes, and introducers. More particularly, the present disclosure relates to biopsy cap configurations providing sealable access for medical instruments to a working channel, such as a working channel for an access port of endoscope.

BACKGROUND

A wide variety of endoscope assemblies, biopsy caps, and seals have been developed. Of the known endoscope assemblies, biopsy caps, and seals, each has certain advantages and disadvantages. There is an ongoing need to provide alternative endoscope assemblies, biopsy caps, and seals as well as methods for making and using the same.

SUMMARY

This disclosure provides design, material, manufacturing method, and use alternatives for medical devices.

An example medical device includes a seal for use in combination with an endoscope, the seal comprising a main body including a circumferential outer wall surrounding a central lumen, the main body having a top surface and a bottom surface, and a plurality of projections extending radially inward from the outer wall towards a center of the lumen, wherein the plurality of projections are arranged in a series of circumferentially and angularly offset layers, wherein each layer includes a plurality of projections.

Alternatively, or additionally to the example above, the plurality of projections define an opening at the center of the lumen, the opening extending axially through the seal.

Alternatively, or additionally to the example above, the series of angularly offset layers extends axially along the main body such that the projections spiral downward around the seal 300 from the top surface to the bottom surface of the main body.

Alternatively, or additionally to the example above, each layer includes the same number of projections.

Alternatively, or additionally to the example above, the plurality of projections in each layer are circumferentially spaced apart.

Alternatively, or additionally to the example above, each layer includes between 3 and 15 projections.

Alternatively, or additionally to the example above, the plurality of projections are arranged in between 3 and 15 layers.

Alternatively, or additionally to the example above, each layer of projections is offset by between 10 and 40 degrees from adjacent layers.

Alternatively, or additionally to the example above, an outer surface of the outer wall includes a plurality of axial slits.

An example method of making a seal for use in combination with an endoscope comprises molding a seal as a single piece element, the seal molded to have a main body including a circumferential wall surrounding a central lumen, and a plurality of projections extending radially outward from the wall away from the lumen, wherein the plurality of projections are molded in a series of circumferentially and angularly offset layers, and turning the molded seal inside out such that the plurality of projections extend radially inward toward a center of the central lumen.

Alternatively, or additionally to the example above, molding the seal includes assembling a multi-piece radially ejectable mold around a core element, wherein the core element defines the shape of the wall and the multi-piece mold defines the shape and orientation of the plurality of projections, wherein molding further includes injection molding the seal and then disassembling the multi-piece mold.

Alternatively, or additionally to the example above, molding the seal includes assembling an axial staked mold including a top and a base and a plurality of plates, wherein each plate defines the shape and orientation of one layer of projections, wherein molding further includes injection molding the seal and then disassembling the axial staked mold.

Another example seal for use in combination with an endoscope comprises a main body including a circumferential outer wall surrounding a central lumen, the main body having a top surface and a bottom surface, at least one support wall extending radially from the outer wall towards a center of the lumen, and at least one helical flap extending from the support wall helically downward along an inner surface of the outer wall, wherein the at least one helical flap defines an opening at the center of the lumen.

Alternatively, or additionally to the example above, the at least one helical flap extends downward in a first direction helically along the inner surface of the outer wall and in a second direction radially towards the center of the lumen.

Alternatively, or additionally to the example above, the at least one support wall consists of only first and second support walls and the at least one helical flap consists of only first and second helical flaps.

Alternatively, or additionally to the example above, the first helical flap extends from a top surface of the first support wall to a bottom surface of a second support wall.

Alternatively, or additionally to the example above, each helical flap has a first end adjacent the top surface of the main body and a second end that extends below the bottom surface of the main body.

Alternatively, or additionally to the example above, the opening is defined in part as a space between the first and second support walls, the space having a first diameter adjacent the top surfaces of the first and second support walls and a second diameter adjacent the bottom surfaces of the first and second support walls.

Alternatively, or additionally to the example above, the first and second support walls are disposed directly opposite one another.

Alternatively, or additionally to the example above, the seal is disposed within a cavity of a biopsy cap, the biopsy cap having a base with a securing member for securing the biopsy cap to a port on the endoscope, the biopsy cap further having a locking member and an outer shell defining the cavity.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
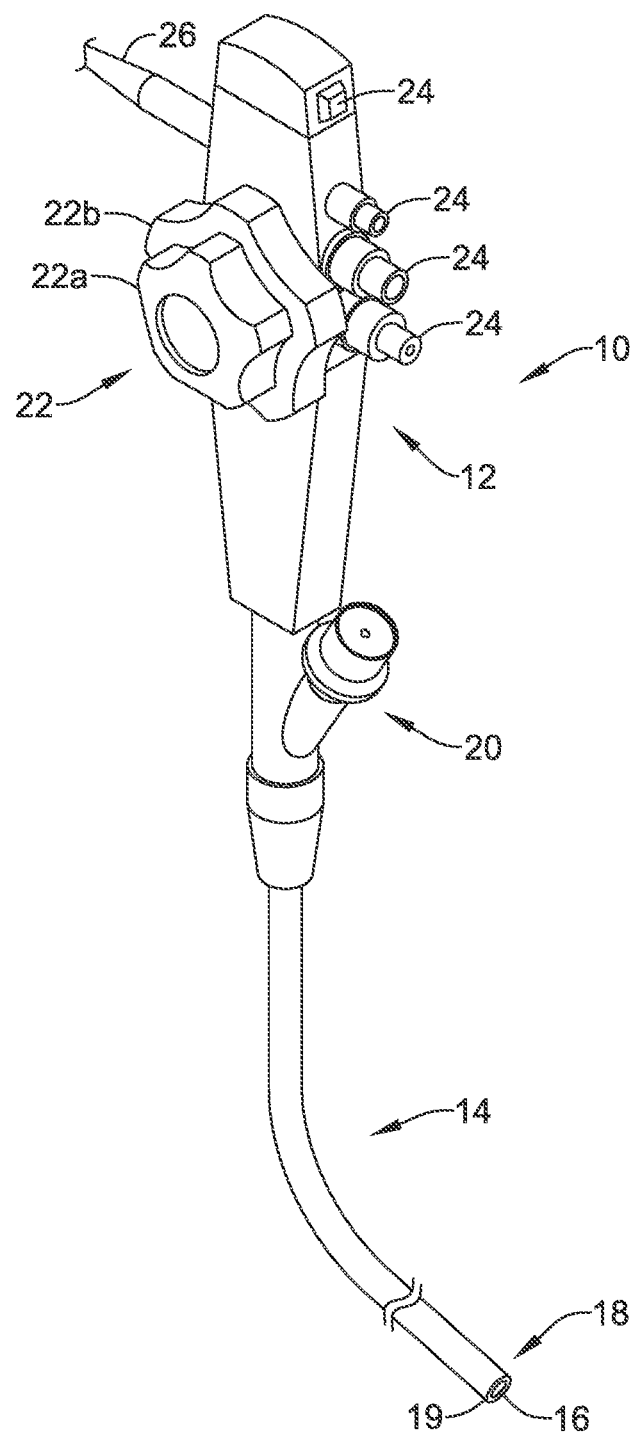
FIG. 1 is a perspective view of an example endoscope assembly with a biopsy cap, according to an embodiment of the present disclosure.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

An example endoscope and/or endoscope assembly 10 is illustrated in FIG. 1. Endoscope 10 may be any of a number of types of endoscopes or related medical devices usually identified by the particular anatomy desired to be reached. For example, endoscope 10 may be a bronchoscope, colonoscope, duodenoscope, esophagoscope, guide tubes, introducers (with or without vision or visualization capabilities), or any other type of endoscope or related medical device. Endoscope 10 may include a handpiece 12 and an elongate shaft 14 extending distally from handpiece 12 to a distal tip 18. Shaft 14 may include a lumen defining a working channel 16 extending through shaft 14 from a distal end 19 near distal tip 18 of shaft 14 to an access port 20 that may be positioned in handpiece 12 or another portion of endoscope 10. Although endoscope 10 is depicted with a single working channel in FIG. 1, it can be appreciated that in other embodiments, endoscope 10 may include multiple working channels, as desired.

Handpiece 12 may include one or a plurality of controls 22, such as rotating knobs, which may be used to control movement of distal tip 18 of shaft 14 during operation. For example, a first rotating knob 22a may control up and down movement or deflection of distal tip 18 of shaft 14, while a second rotating knob 22b may control side-to-side movement or deflection of distal tip 18 of shaft 14. Handpiece 12 may also include one or a plurality of buttons 24, which may be used to activate suction or deliver fluid such as air, saline and/or water, etc. through a lumen of the endoscope 10 or perform other functions as desired. Additionally, handpiece 12 may include an optical cable 26 connected to an external light source (not shown).

Figure 2:
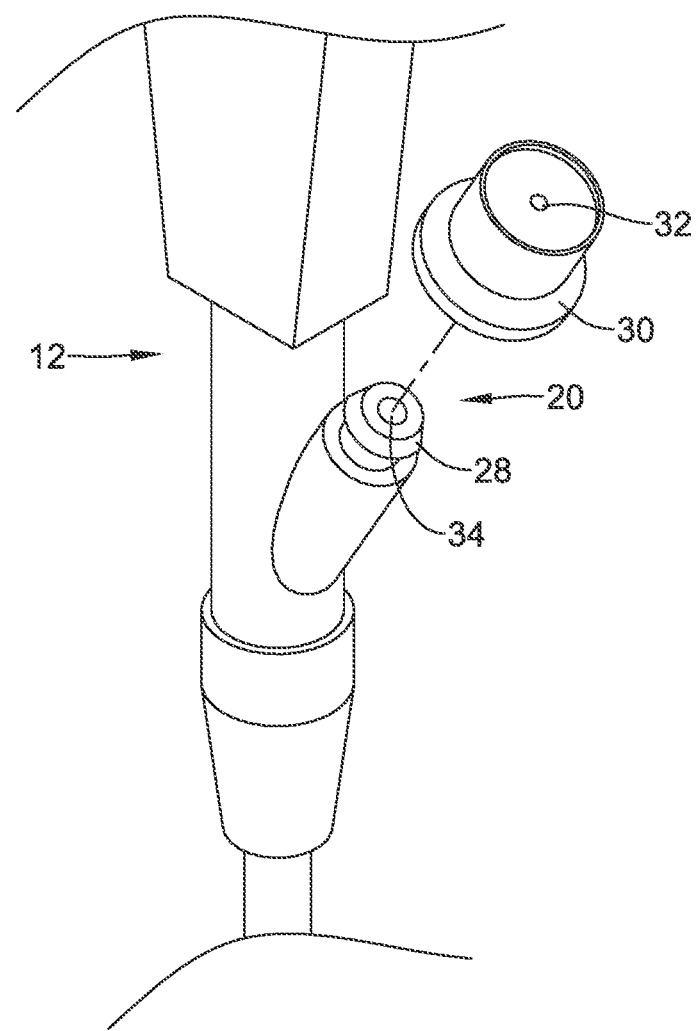
FIG. 2 is an exploded view of a portion of the example endoscope assembly shown in FIG. 1 illustrating the biopsy cap, according to an embodiment of the present disclosure.

Turning now to FIG. 2, here access port 20 of handpiece 12, which provides access to working channel 16 of endoscope 10, is illustrated. Access port 20, which may extend from the side of endoscope 10 or at another location, may include a coupling portion 28 for coupling a cap 30 to access port 20. Cap 30, which may be removably attached or permanently attached to access port 20, may provide access for inserting and/or advancing an endoscopic device through working channel 16 of endoscope 10.

Caps like cap 30, which may be termed "biopsy caps", are often designed with several functions in mind. For example, cap 30 may form a fluid/air barrier to working channel 16 that may help control insufflation and bile fluid egress therefrom that later have the potential to spill onto the clinician's hands and/or the floor thereby interfering with the intervention and/or become a biohazard. In addition, cap 30 may have an opening 32 extending therethrough. Opening 32 may be in fluid communication with working channel 16 and it may reduce the size of the opening 34 of working channel 16, for example, to accommodate an endoscopic device or instrument. Thus, caps like cap 30 may be much like an adapter in that it forms a physical transition at opening 34 of working channel 16 (or other instrument channels or access points) so that it transitions to a size more closely to that of the device to be inserted into working channel 16. Some additional discussion regarding biopsy caps can be found in U.S. Pat. No. 9,149,173, filed Jun. 20, 2006 and titled "Medical Device For Use In Endoscopic Procedure," U.S. patent application Ser. No. 11/405,655, filed Apr. 17, 2006 and titled "Elongate Medical Devices Having An Improved Distal Profile For Use With An Endoscope," and to U.S. patent application Ser. No. 11/400,806, filed Apr. 7, 2006 and titled "Biopsy port for easy device passage," the disclosures of which are herein incorporated by reference in their entirety and for all purposes.

In various embodiments, features and advantages of providing sealable access to a working channel, e.g., of an endoscope, may be realized in combination with a biopsy cap and biopsy cap housing. Such sealable access to a working channel, which may be reinforced, may be implemented with features throughout the disclosures of United States Patent Application Publication 2019/0046016, filed on Aug. 10, 2018 and titled "Biopsy Cap For Use With Endoscope"; United States Patent Application Publication 2020/0138274, filed on Nov. 1, 2019, and titled "Attachments For Endoscopes"; United States Patent Application Publication No. 2020/0138419, filed on Nov. 1, 2019, and titled "Biopsy Cap And Biopsy Cap Housing"; United States Patent Application Publication No. 2020/0138272 filed on Nov. 1, 2019, and titled "Devices, Systems, And Methods For A Biopsy Cap And Housing"; United States Patent Application Publication No. 2020/0138277, filed on Nov. 1, 2019, and titled "Devices, Systems, And Methods For Providing Sealable Access To A Working Channel"; United States Patent Application Publication No. 2020/0138276, filed on Nov. 1, 2019, and titled "Devices, Systems, and Methods for Providing Sealable Access to a Working Channel," all of which applications are each hereby incorporated by reference herein in their entirety and for all purposes.

A number of additional biopsy caps are contemplated that incorporate at least some of the desirable features of biopsy caps as well as have other desirable characteristics. The description discloses some of the embodiments of caps that are contemplated. These caps may include a passive seal. For the purposes of this disclosure, a passive seal is a seal that seals endoscope 10 at port 20 (e.g. of FIG. 1) so as to prevent the leakage of bodily fluids and/or air. In addition, by virtue of being "passive", the seals disclosed herein are configured to seal off endoscope 10 at port 20 without the need of any so-called "active" processes or steps by the clinician.

Figure 3:
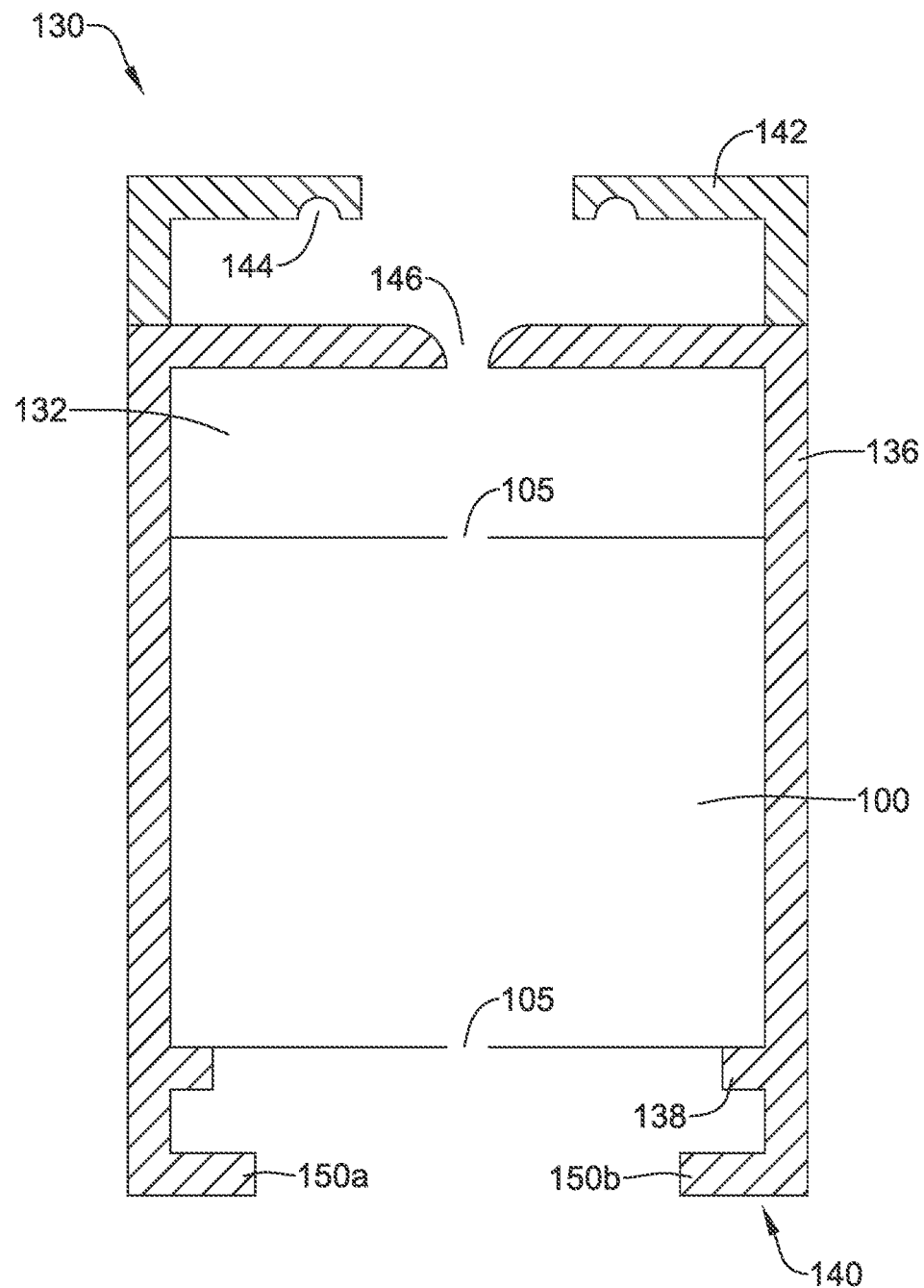
FIG. 3 is a cross-sectional view of a biopsy cap, according to an embodiment of the present disclosure.

Turning now to the remaining figures, FIG. 3 illustrates an example biopsy cap 130 that may include an outer shell 136 defining an inner chamber 132, a securing member 140 that may help to secure cap 130 to port 20 (e.g., of FIG. 1), one or more locking members 142 coupled to shell 136, and an inner seal member 100 disposed within outer shell 136. Outer shell 136 may take a number of different shapes and forms. In general, however, outer shell 136 may be made from a relatively rigid or hard polymer/plastic, a metal or metal alloy, a ceramic, and the like, or combinations thereof and may take a form resembling an exoskeleton or protective covering over the more delicate interior (e.g., seal member 100). In addition, by virtue of forming outer shell 136 from a relatively rigid material, a number of accessories to and/or structural components of cap 130 may be secured to or integrally formed with shell 136. For example, securing member 140 and/or locking members 142 may be secured to or integrally formed with outer shell 136.

Outer shell 136 may have one or more apertures 146 formed therein. Aperture 146, for example, may be disposed on a top surface or surface that is opposite securing member 140, although any other suitable portion of outer shell 136 may include aperture 146 including the sides or side surfaces. Aperture 146 may be the entrance point or otherwise define one or more openings that extend through the inner chamber 132 of the cap 130 and into working channel 16 (e.g., of FIG. 1) when cap 130 is seated on port 20. For example, aperture 146 may extend through outer shell 136 and provide access to the seal member 100. Thus, aperture 146 may form the exterior opening in cap 130 where other medical devices (e.g., guidewires, catheters, etc.) can be passed through so as to gain access to working channel 16 via seal member 100. Cap 130 may include a flange 138 extending into the inner chamber 132. The seal member 100 may sit on the flange 138. Seal member 100 may have openings 105 in top and bottom surfaces thereof which may be aligned longitudinally with the aperture 146 in the cap 130. Aperture 146 may guide the medical devices into the opening 105 and through the seal member 100.

To ease the ability of a user to pass a medical device through aperture 146, aperture 146 may have a chamfered or beveled edge, which may function like a funnel to guide the medical device into the aperture 146 and may assist the ability of a user to pass a medical device through the aperture 146. In addition to the funneling function that may be realized by the inclusion of beveled aperture 146, aperture 146 may also provide cap 130 with a number of additional desired characteristics. For example, because aperture 146 is formed in the relatively rigid outer shell 136 and because aperture 146 is generally positioned a distance away from port 20 (e.g., in FIG. 1), aperture 146 and/or outer shell 136 may also function as a strain relief that may relieve strain that might otherwise be applied to endoscope 10 (e.g., at port 20), for example, during device exchanges or transfers. Thus, the shear stress that may be generated during device exchanges can be shifted away from endoscope 10, which may improve the ability of cap 130 to maintain a good seal at port 20.

Securing member 140 may be disposed on a bottom surface of cap 130. Securing member 140 may take any number of a wide array of forms including those disclosed herein. For example, securing member 140 may include a pair of tabs 150a/150b, which may snap onto or otherwise secure to port 20 (e.g., in FIG. 1). Securing tabs 150a/150b onto port 20 may include, for example, snapping tabs 150a/150b onto a narrowed ring or portion of port 20. This may include snapping tabs 150a/150b onto port from a peripheral or side region of port 20. In addition, a portion of shell 136 may include a cutout or notch (not shown) that may provide some structural relief for securing member 140 and that may allow tabs 150a/150b to have greater flexibility when securing cap 130 to port 20 than without the relief. The precise form of securing member 140 and/or tabs 150a/150b may vary. For example, a different number of tabs may be utilized, differently shaped tabs may be utilized or a different securing system altogether may be utilized for securing cap 130 to port 20. Furthermore, various adaptors may be provided to create a suitable connection between cap 130 and port 20 if such a connection cannot be easily made with tabs 150a/150b or another suitable securing member 140.

Locking members 142 may be generally disposed adjacent the top surface of cap 130 and they may be used to secure and/or hold the position of a device (e.g., a guidewire, catheter, etc.) extending through cap 130 into working channel 16. However, locking members 142 may be disposed on any suitable surface of cap 130 and/or shell 136. Locking members 142 may also be integrally formed with shell 136. In addition to holding the position of a device, locking members 142 may also tend to guide these devices away from the center of cap 130 so that other device may gain access to working channel 16 via cap 130. In at least some embodiments, locking members 142 may include one or more bends, hooks, or channels 144 formed therein that a medical device may be wrapped around or pressed against to hold its position. The number of locking members 142 may vary. In some embodiments, one locking member 142 is utilized. In other embodiments, two, three, four, five, six, or more locking members 142 are utilized. In addition, the precise form of locking members 142 may also vary. For example, locking member 142 may or may not include a wing or flap that may tend to direct a device toward locking member 142.

Figure 4:
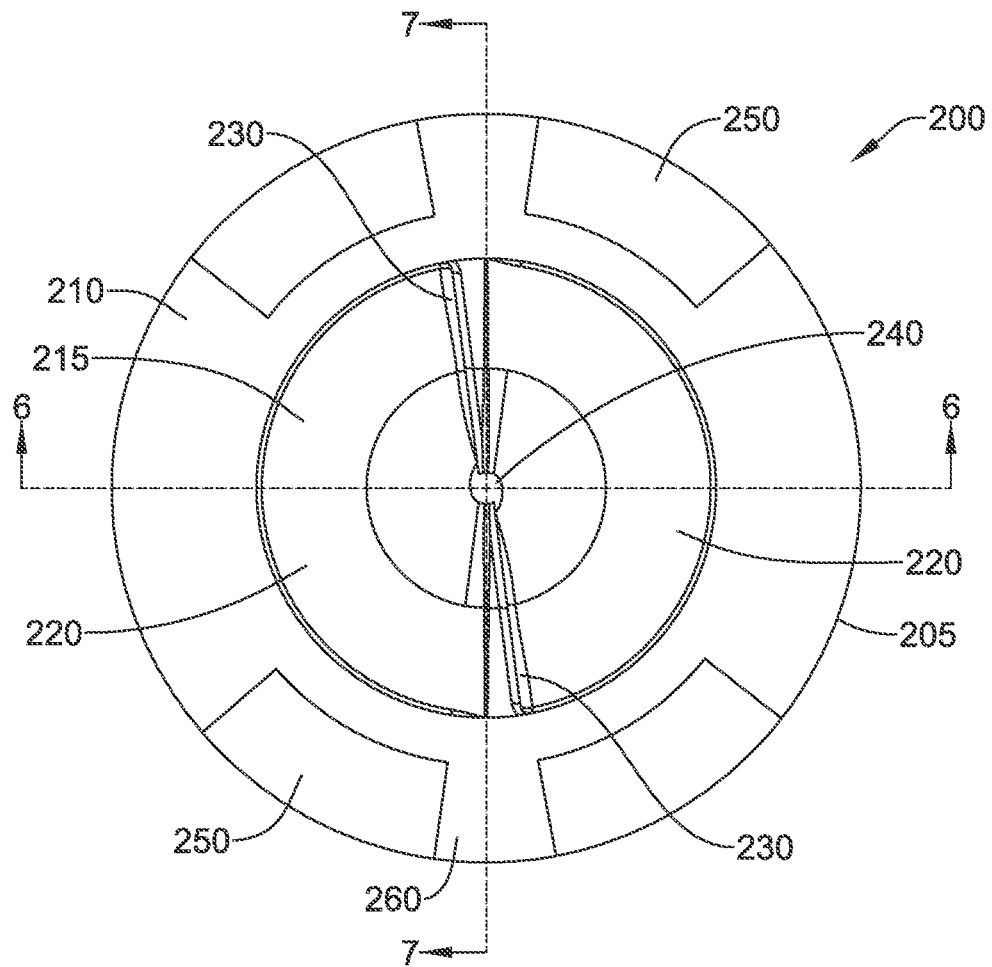
FIG. 4 is a top view of a seal member, according to an embodiment of the present disclosure.
Figure 5:
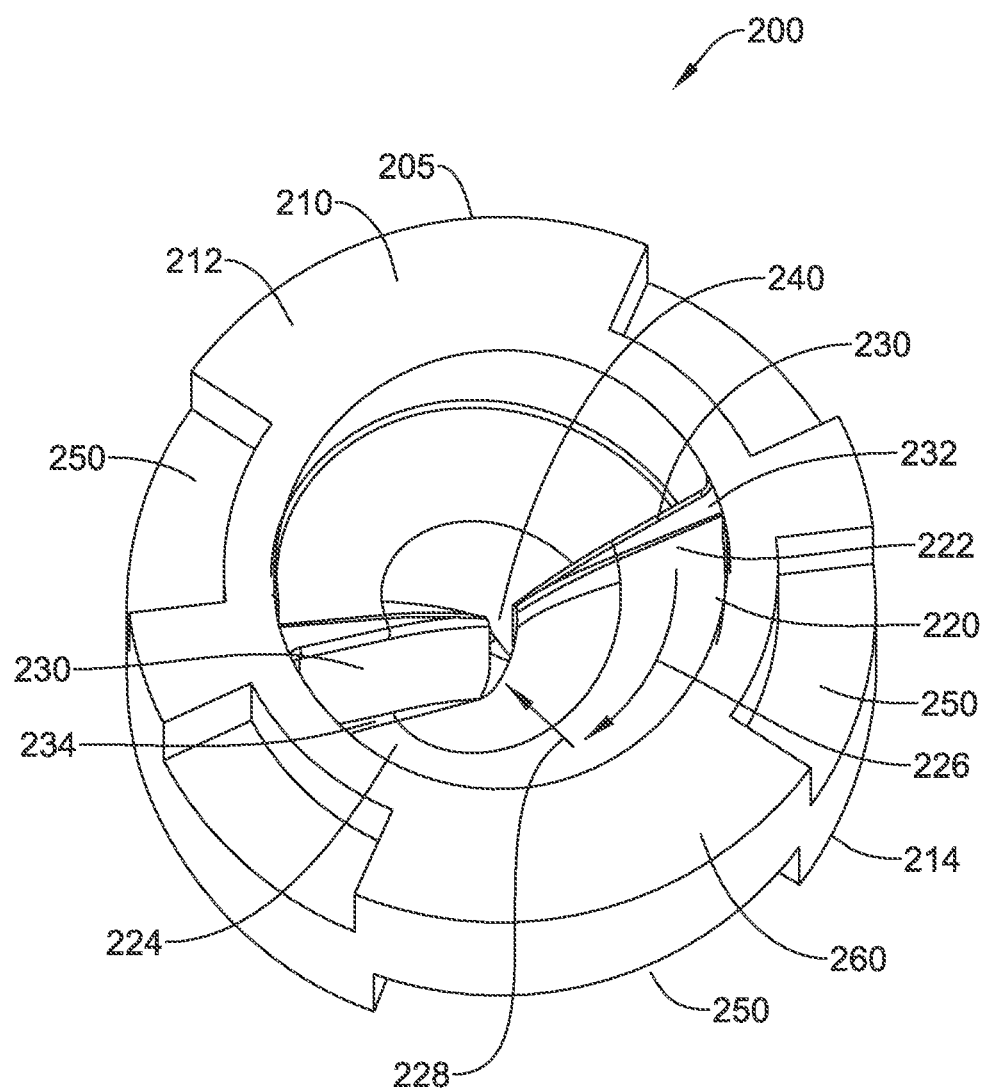
FIG. 5 is perspective top view of the seal member of FIG. 4.

FIG. 4 is a top view of an example seal member 200 that may be disposed within the cap 130 shown in FIG. 3. The seal member 200 may include a main body 205 defined by a circumferential outer wall 210 surrounding a central lumen 215. At least one axial support wall 230 may extend radially from the outer wall 210 into the central lumen 215. At least one helical flap 220 may extend from the top surface 232 of the support wall 230 helically downward along an inner surface of the outer wall 210 to a bottom surface 234 of the support wall 230, as shown in FIG. 5. The helical flap 220 and the support wall 230 do not extend all the way to the center of the lumen 215 but leave an opening 240 that extends completely through the seal member 200. Accordingly, medical device(s) may be advanced through aperture 146 in the cap 130 shown in FIG. 3, into the lumen 150 in the seal member 200, through opening 240, and into working channel 16 for use as part of a medical intervention. Alternatively, the helical flap 220 and the support wall 230 may extend to the center of the lumen 215 while allowing an instrument to pass through the lumen 215 (e.g., by the helical flap 220 and/or the support wall 230 flexing and/or tearing).

In the embodiment shown in FIGS. 4 and 5, the seal member 200 includes only two support walls 230 disposed opposite one another, and only two helical flaps 220, each extending helically from one of the two support walls 230. Each helical flap 220 may extend from a first end 222 at the top surface 232 of the support wall 230, helically downward to a second end 224 at the bottom surface 234 of the opposite support wall 230, as shown in FIG. 5. The downward direction may be defined as extending from a top surface 212 to a bottom surface 214 of the main body 205. Each helical flap 220 may extend downward in two directions: helically along the outer wall 210 in the direction shown by first arrow 226, and radially towards the opening 240 in the direction shown by second arrow 228. The downward sloping helical flaps 220 may help guide or funnel devices through the opening 240. The support walls 230 may extend vertically, along a longitudinal axis extending through the opening 240. The two support walls 230 may be disposed opposite each other, with the helical flaps 220 each defining substantially half of the circular seal member 200.

The embodiment shown in FIGS. 4-5, with only two support walls 230 and only two helical flaps 220 may provide an advantage over seal members with more than two support walls and helical flaps. For example, the inclusion of only two support walls 230 and two helical flaps 220 may allow for an increased thickness of the flaps along their cross-section by 10-20% which my improve sealing performance. Further, the number of potential pockets formed at the bottom of the flap and support wall is reduced. These pockets may become deeper when the angle between the flap and support wall is lower. Reducing the number of support walls and flaps to only two results in a reduced pocket depth because the angle between the flap and support wall increases, which significantly reduces the occurrence of device obstruction and improves the ability of devices to translate through the seal member 200.

The outer wall 210 of the seal member 200 may include a series of alternating grooves 250 and legs 260 in both the top and bottom surfaces. The grooves 250 and legs 260 allow two or more seal members to be stacked (e.g., axially with each other). In some embodiments, the grooves 250 and legs 260 may be uniformly sized and equally spaced around the outer wall 210 (not shown), allowing two seal members 200 to be stacked in any of four 90 degree offset orientations. For example, with the two opposing support walls 230 of each seal member 200 stacked over each other (a "minus" or dash symbol configuration that is the same when one seal member is rotated 180 degrees), and with the two opposing support walls 230 of one seal member 100 oriented perpendicular to the support walls 230 of the second seal member 200 (a "plus" or cross symbol configuration that is the same when one seal member is rotated 90 degrees). In other embodiments, the grooves 250 and legs 260 may be spaced non-equidistant (see FIG. 5) and sized such that two seal members 200 may be stacked in only two 180 degree offset orientations. Sizing and spacing the grooves 250 and legs 260 such that two seal members 200 can only be stacked in the "plus" configuration provides better sealing with similar passability performance of medical devices through the seal members 200 as compared to the "minus" configuration.

Figure 6:
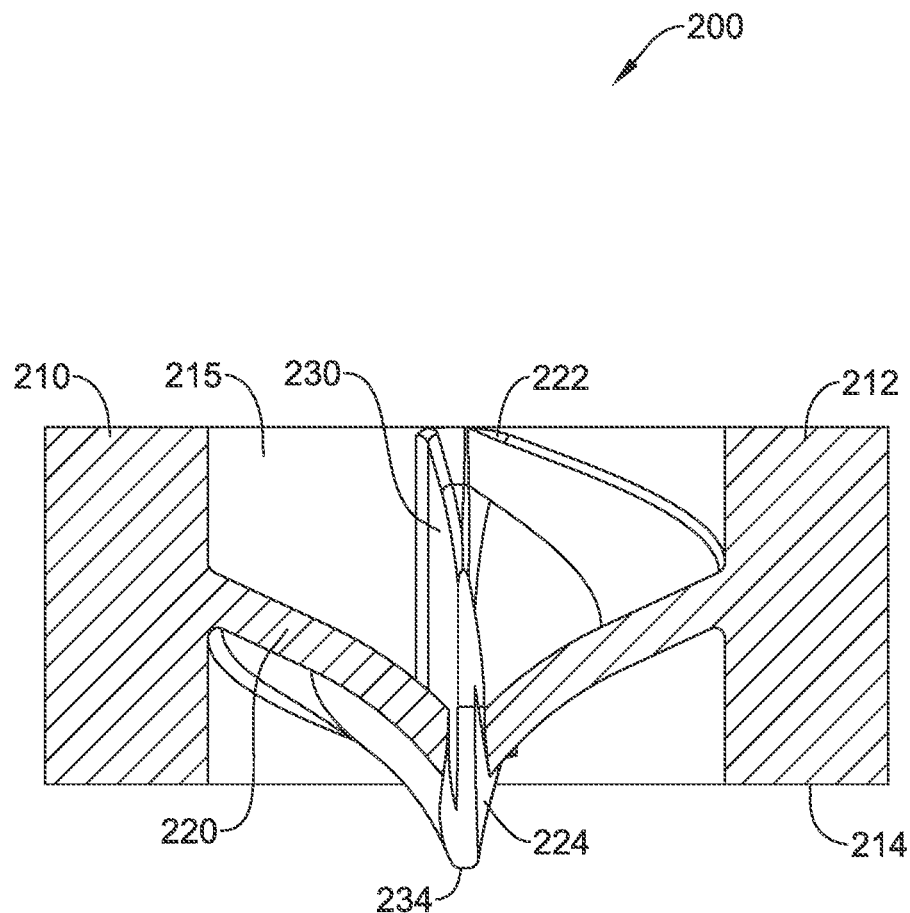
FIG. 6 is a cross-sectional side view of the seal member of FIGS. 4 and 5, taken along line 6-6.
Figure 7:
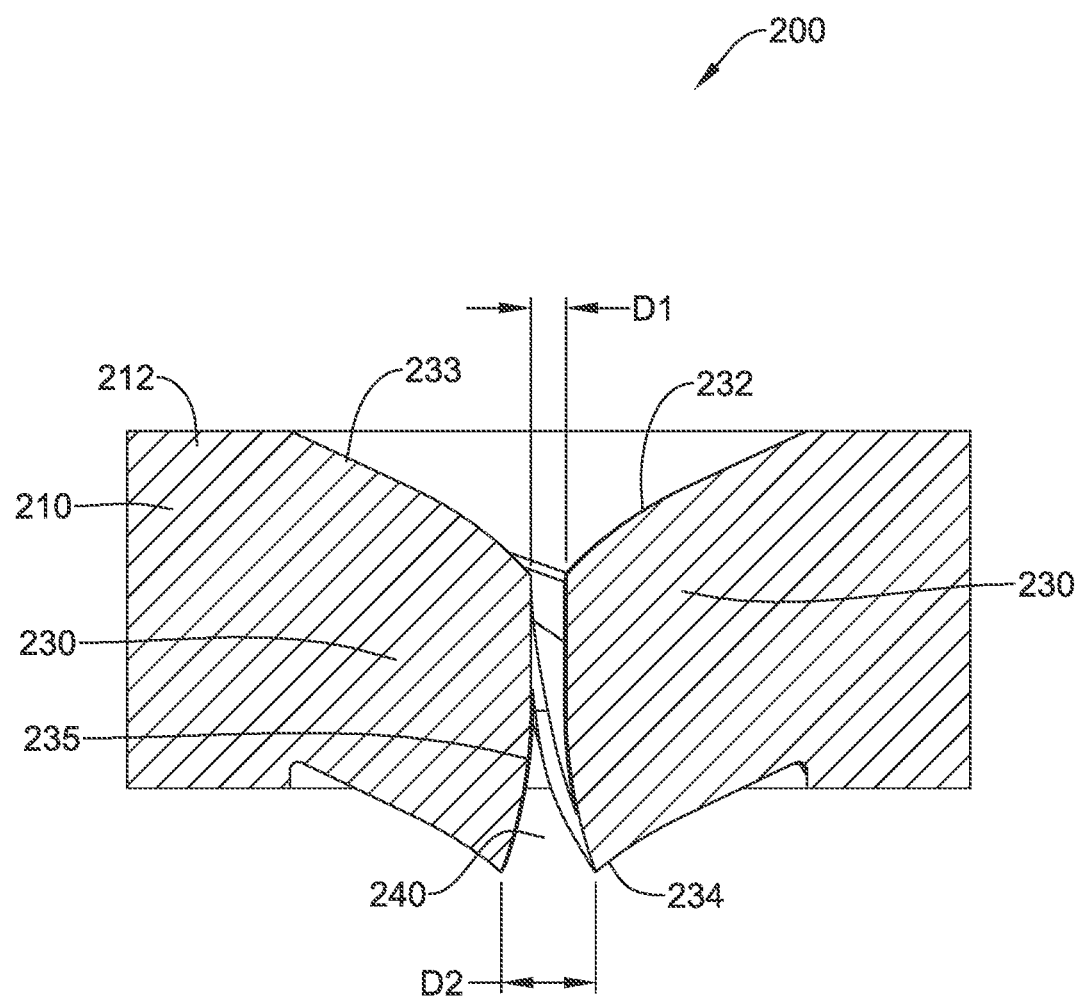
FIG. 7 is a cross-sectional side view of the seal member of FIGS. 4-6, taken along line 7-7.

The cross-sectional view in FIG. 6 illustrates the helical flaps 220 extending helically downward from the first end 222 at the top surface 212 of the main body 205 to the second end 224 adjacent the bottom surface 234 of opposite support wall 230. The bottom surface 234 of each support wall 230 extends below the bottom surface 214 of the seal member 200. FIG. 7 shows the cross-sectional view rotated 90 degrees from FIG. 6, taken through each of the opposing support walls 230. In FIG. 7, the variable diameter of the opening 240 adjacent the support walls 230 is shown. The support walls 230 may angle downward from a base 233 connected to the outer wall 210 to an inner edge 235 that partially defines the opening 240. The opening 240 increases from a first diameter D1 between facing support walls 230 adjacent the top surface 232 of the support walls 230 to a second diameter D2 at the bottom surface 234 of the support walls 230. The increasing hole diameter at bottom of the seal member 200 prevents the formation of a pocket which may obstruct the introduction of a curved tip medical device. The reduced diameter D1 at the top compensates for the larger bottom diameter D2 of the opening 240, thus maintaining the sealing properties of the seal member 200.

The seal member 200 illustrated in FIGS. 4-7 may be a single monolithic piece formed by injection molding or other suitable molding techniques. The seal member 200 may be made of an elastomeric material such as a flexible silicone.

Figure 8:
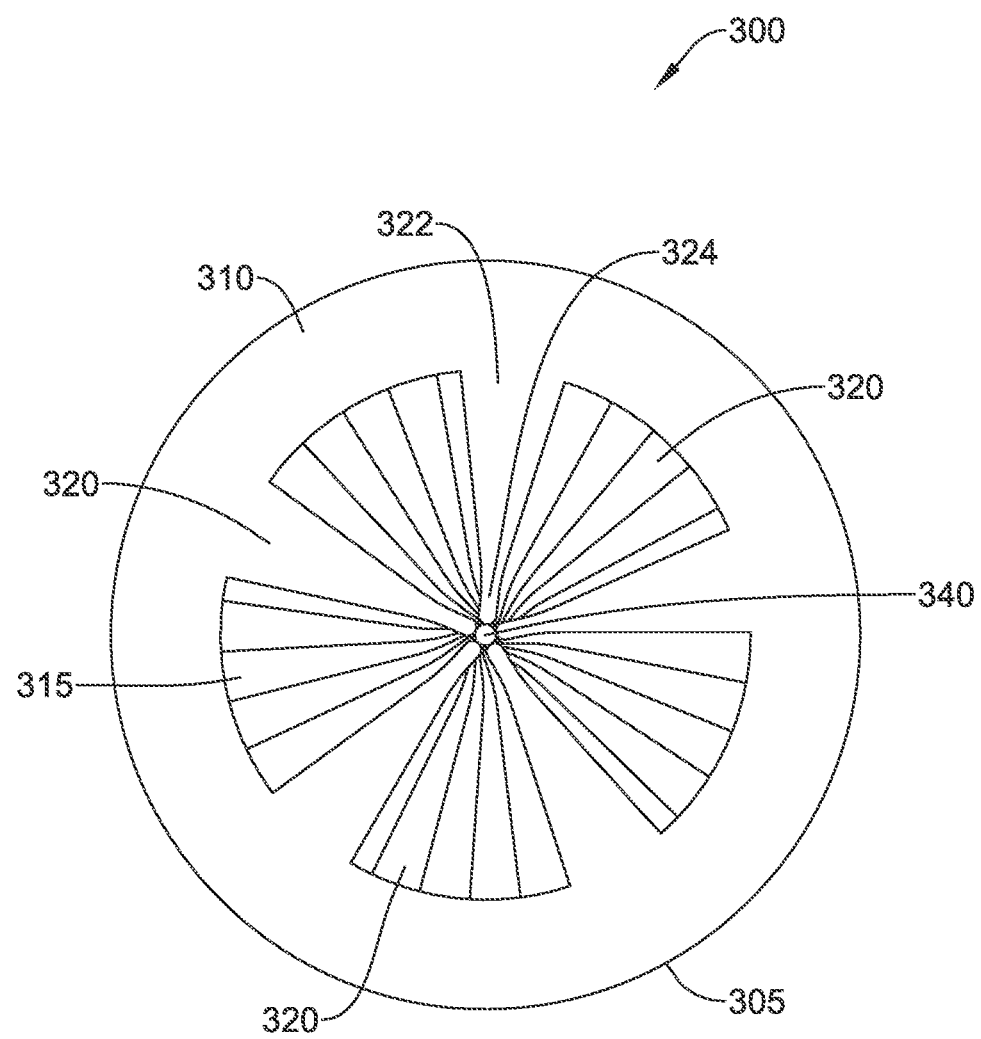
FIG. 8 is a top view of another example seal member, according to an embodiment of the present disclosure.

FIG. 8 shows a top view of another example seal member 300 that may be disposed within the cap 130 shown in FIG. 3. The seal member 300 may include a main body 305 defined by a circumferential outer wall 310 surrounding a central lumen 315. A plurality of projections 320 may extend radially inward from the outer wall 310 towards a center of the lumen 315. The projections 320 may extend from a base 322 attached to the outer wall 310 to a tip 324. The tips 324 of the projections 320 do not meet at the center of the lumen 315 but leave an opening 340 that extends completely through the seal member 300. Accordingly, medical device(s) may be advanced through aperture 146 in the cap 130 shown in FIG. 3, through opening 340, and into working channel 16 for use as part of a medical intervention. Alternatively, the helical projections 320 may extend to the center of the lumen 315 while allowing an instrument to pass through the lumen 315 (e.g., by the projections 320 flexing and/or tearing).

Figure 9:
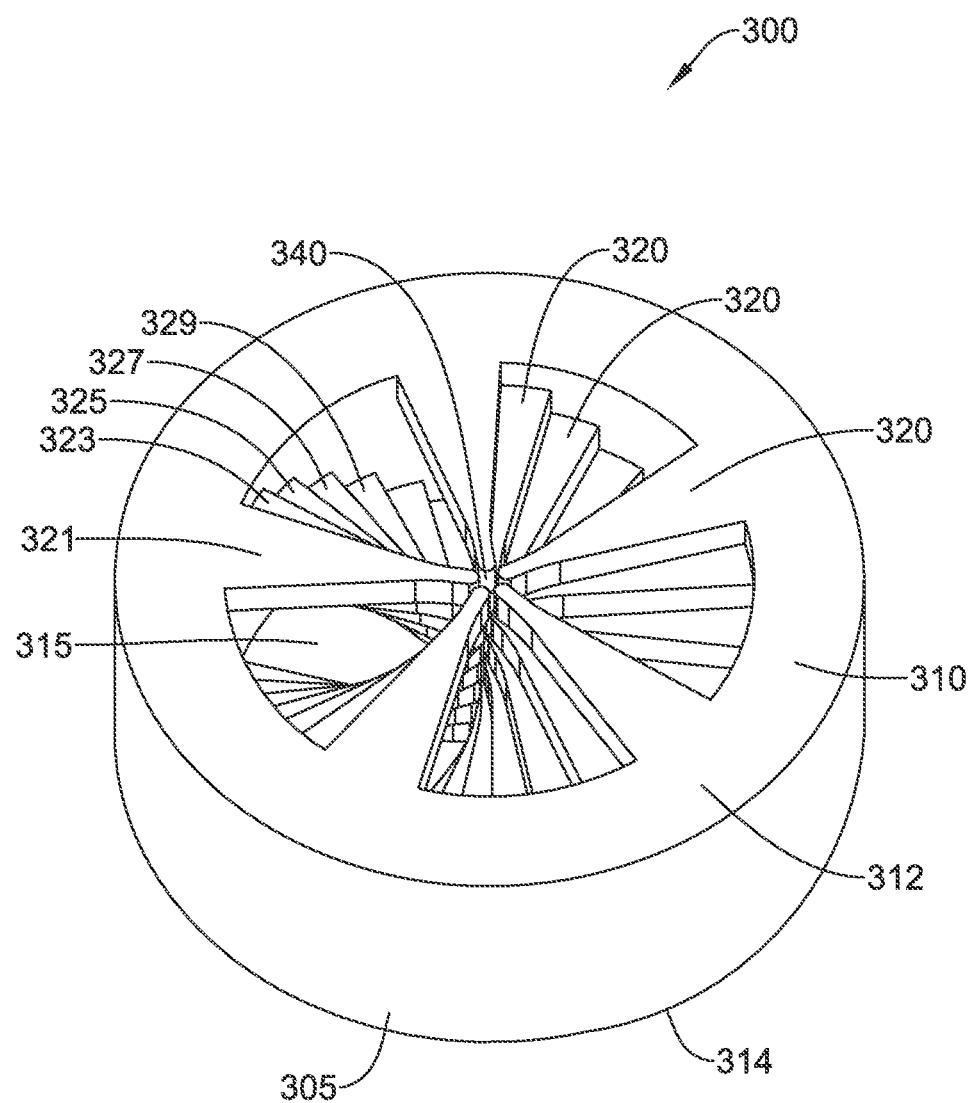
FIG. 9 is a perspective top view of the seal member of FIG. 8.

The plurality of projections 320 may be oriented in a series of circumferentially and angularly offset layers such that they spiral downward around the seal member 300 from the top surface 312 to the bottom surface 314 of the outer wall 310, in a staircase manner as shown in FIG. 9. Each layer may include a plurality of circumferentially spaced apart projections 320. The series of offset layers may extend axially along the main body 305 with a first layer 321 defining a portion of the top surface 312 of the main body, a second layer 323 disposed under and circumferentially offset from the first layer 321, a third layer 325 disposed under and circumferentially offset from the second layer 323, a fourth layer 327 disposed under and circumferentially offset from the third layer 325, a fifth layer 329 disposed under and circumferentially offset from the fourth layer 327, etc. The bottom layer may define a portion of the bottom surface 314 of the main body 305.

The seal member 300 may include any number of projections 320. In some embodiments, the seal member 300 may include a plurality of layers each including three to fifteen circumferentially spaced apart projections 320 arranged equidistant around the circumference of the main body 305. The seal member 300 may include three to fifteen layers of projections. In the example shown in FIG. 9, the main body 305 includes seven layers each having five projections.

Figure 10:
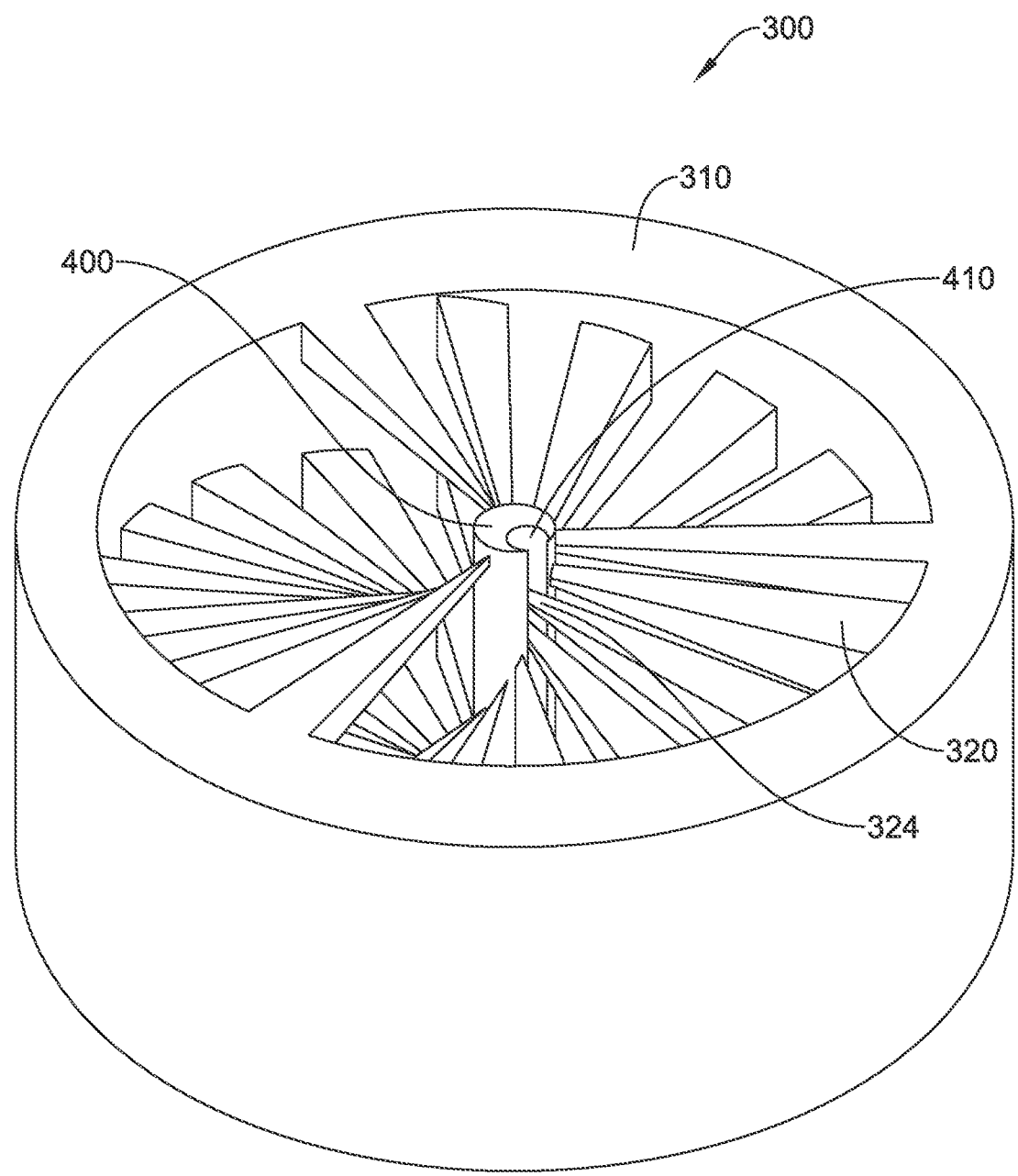
FIG. 10 is a perspective top view of the seal member of FIGS. 8 and 9 with a medical device inserted therethrough.

When a medical device is inserted through the opening 340 in the seal member 300, the tips 324 of the projections 320 may engage the medical device to form a seal. The seal member 300 may provide an improved seal against a catheter or other medical device having a longitudinal slit or channel, especially a C shaped longitudinal channel. When a device 400 having a C-shaped channel 410 is inserted through the opening in the seal member 300, the tips 324 of the projections 320 may enter the channel 410 of the device 400, providing an enhanced seal, as shown in FIG. 10. The plurality of projections 320 disposed circumferentially around the outer wall 310 and extending radially inward provides the advantage of engaging the channel 410 regardless of the rotational orientation of the device 400. Also, when the device 400 is rotated while disposed in the seal member 300, the channel 410 will remain sealed because while some projection tips 324 will slip out of the channel 410 as the device 400 rotates, adjacent projection tips 324 will enter and seal the channel 410. In some embodiments, the projection tips 324 may be sized and shaped to match the dimensions of the channel 410 of a particular device 400.

Figure 11:
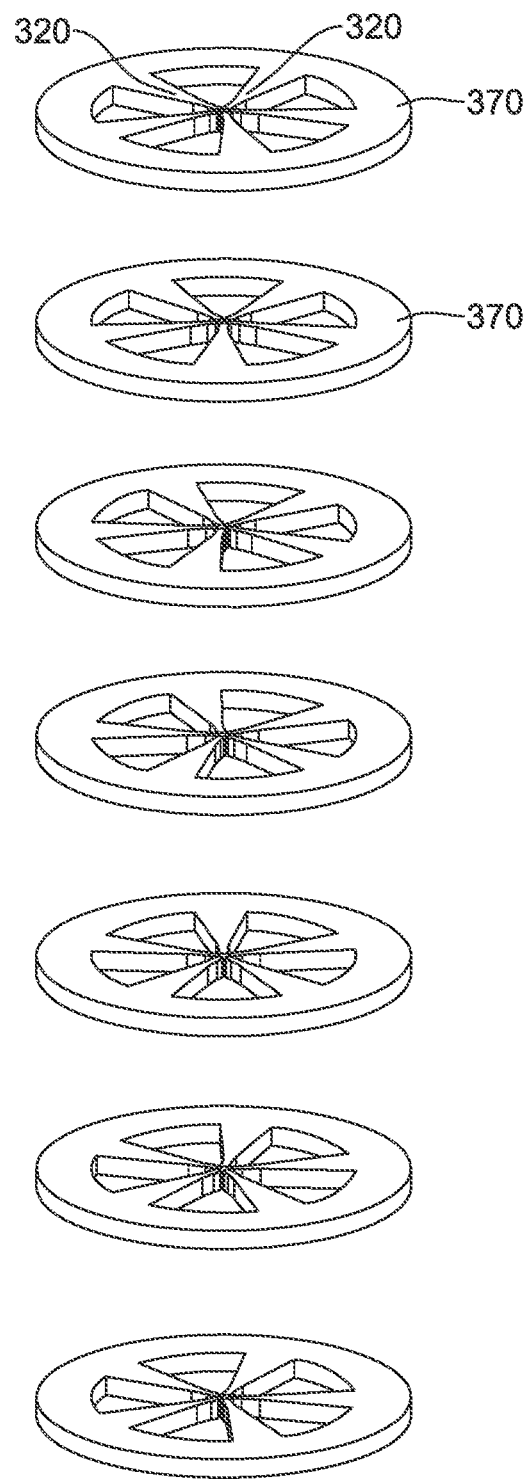
FIG. 11 is a perspective view of separate discs used to manufacture or assemble the seal member of FIGS. 8-10, according to an embodiment of the present disclosure.

The seal member 300 may be manufactured using a variety of methods. In one example, the seal member 300 may be molded as a plurality of separate discs 370 as shown in FIG. 11. In some examples, each disc 370 may be molded with, e.g., 5 projections 320 (although other numbers of projections 320 are contemplated as discussed above) each having a tip 324 with a dimension sized to engage the C-channel. The discs 370 may be stacked one above another with each disc clocked at an angle to cover the entire 360° periphery around the opening 340. The stacked discs may then be bonded together to form the seal member 300. While this stacking process results in a seal member 300 having the desired sealing properties, the method of individually molding each disc and then assembling them into the seal member 300 may be time-consuming as this method calls for expensive assembly automation process, since manual assembling is not feasible. Additionally, controlling the angular orientation of each disc during assembly may be expensive and challenging. All of these factors may bring up the cost of assembly and reduce yield.

Molding the seal member 300 with all projections 320 facing inward in a single molded component, however, may be difficult due to the many needed undercuts and restriction of tool movement. Additionally, dissolving core-molding process may increase the cost and impact the quality of the component.

Figure 12:
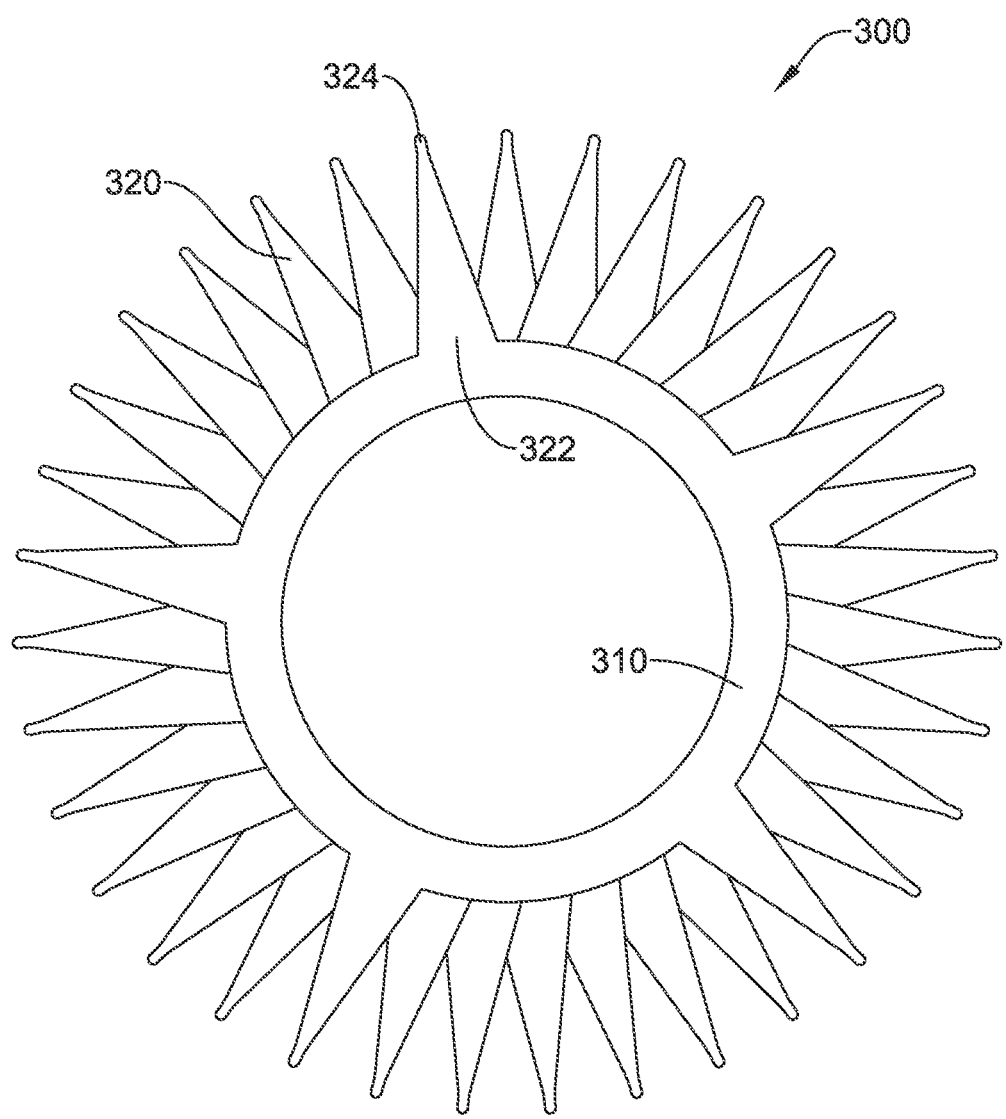
FIG. 12 is a top view of an example seal member after molding and before being turned inside out, according to an embodiment of the present disclosure.
Figure 13:
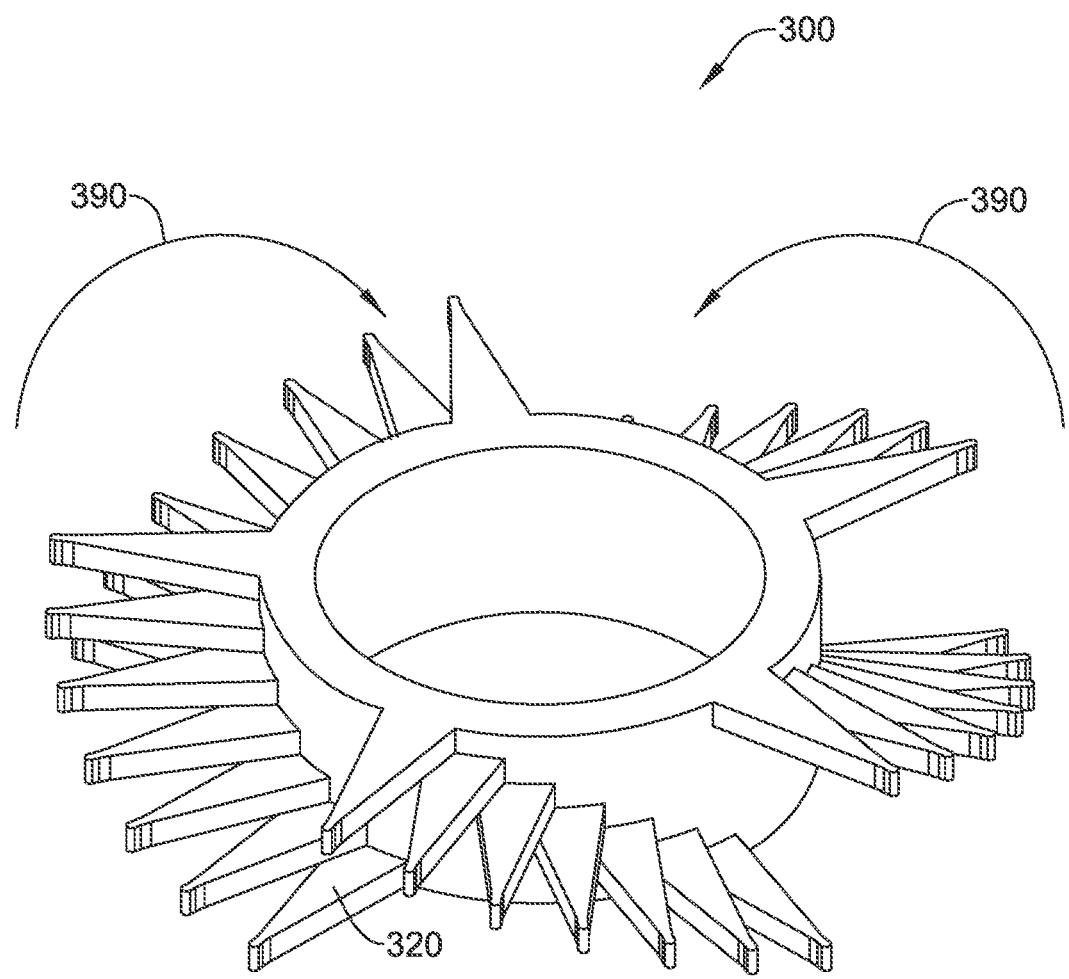
FIG. 13 is a perspective view of the seal member of FIG. 12.
Figure 14:
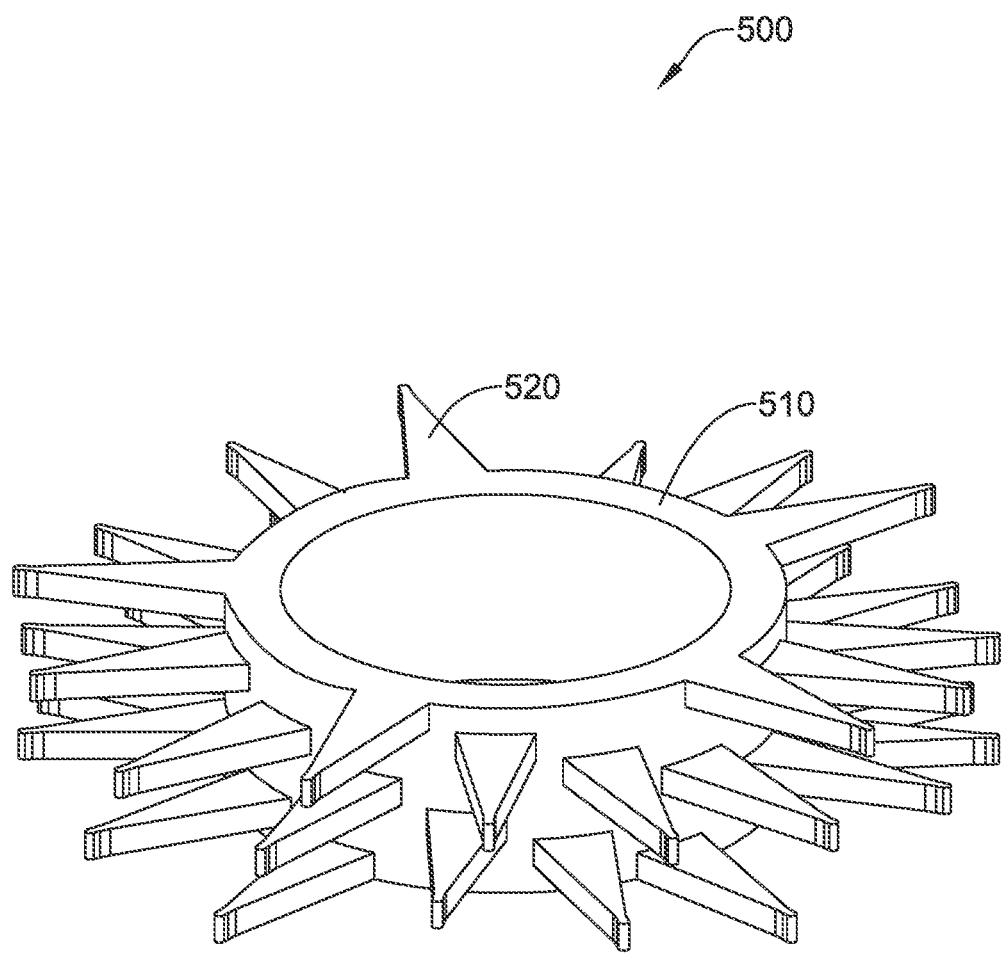
FIG. 14 is a perspective view of a seal member after molding and before being turned inside out, according to an embodiment of the present disclosure.

In another example, the entire seal member 300 may be molded in a single monolithic piece in a simple, cost-effective process. The seal member 300 may be molded with the base 322 of all the projections 320 disposed on the outer periphery of the outer wall 310 and the tips 324 of the projections 320 extending radially outward, as shown in FIG. 12. The projections 320 may be arranged in a series of circumferentially offset layers. In the example shown in FIG. 13, each layer has five projections 320 and there are seven layers of projections, with each layer offset circumferentially from the layers above and below. This orientation forms a staircase of projections 320. After unmolding, the seal member 300 is turned inside out, turning the projections 320 in to the center, as indicated by arrows 390. The resulting structure is as shown in FIG. 9. The layers of projections 320 may be offset in a variety of patterns. In some embodiments, each layer of projections may be offset circumferentially by between 5 and 40 degrees from adjacent layers. In the example shown in FIG. 13, the layers of projections may be offset circumferentially by 11 degrees from the adjacent layers above and/or below. In another example, shown in FIG. 14, a seal member 500 may have seven layers of projections 520 offset circumferentially by 22 degrees from the adjacent layers above and/or below.

Figure 15:
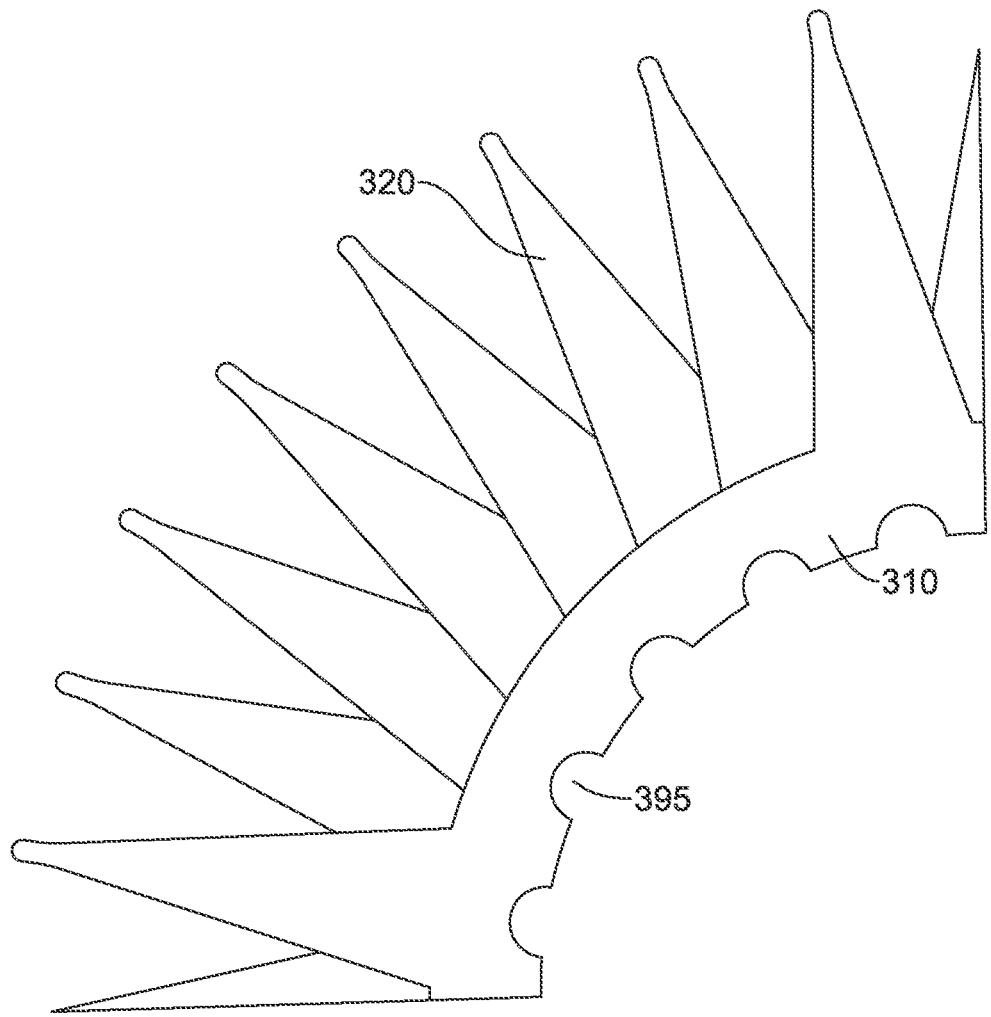
FIG. 15 is a partial top view of a seal member after molding and before being turned inside out, according to an embodiment of the present disclosure.

In some examples, the outer wall 310 may include one or more axial grooves or slits 395 formed on the inner surface during molding, as shown in FIG. 15. The slits 395 are on the outer surface of the outer wall 310 after the seal member 300 is turned inside out and may provide stress relief for the completed seal member 300. The slits 395 may prevent warping of the seal member 300 after it is turned inside out.

Figure 16:
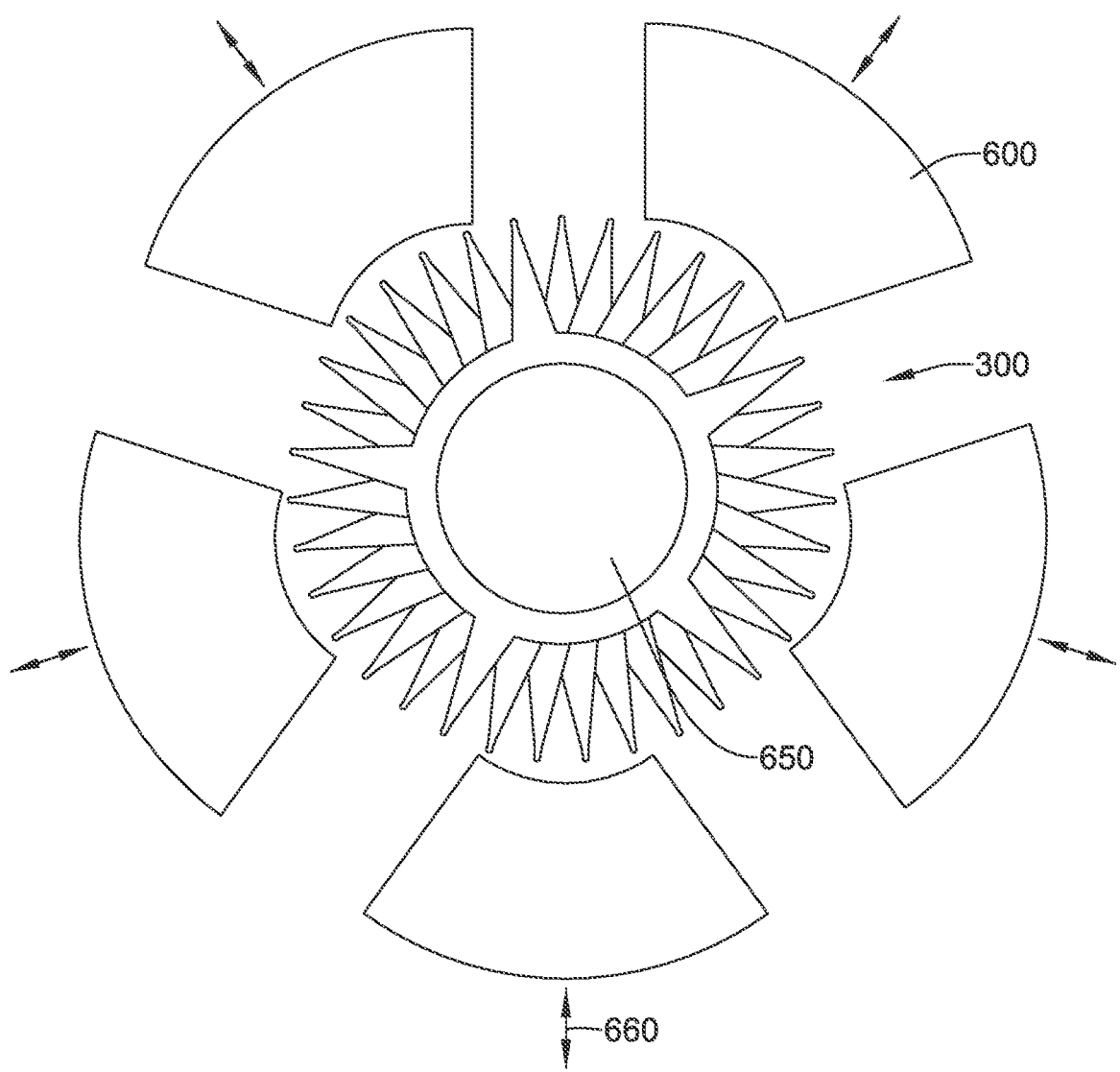
FIG. 16 is a top view of a mold with a seal member disposed therein, according to an embodiment of the present disclosure.
Figure 17:
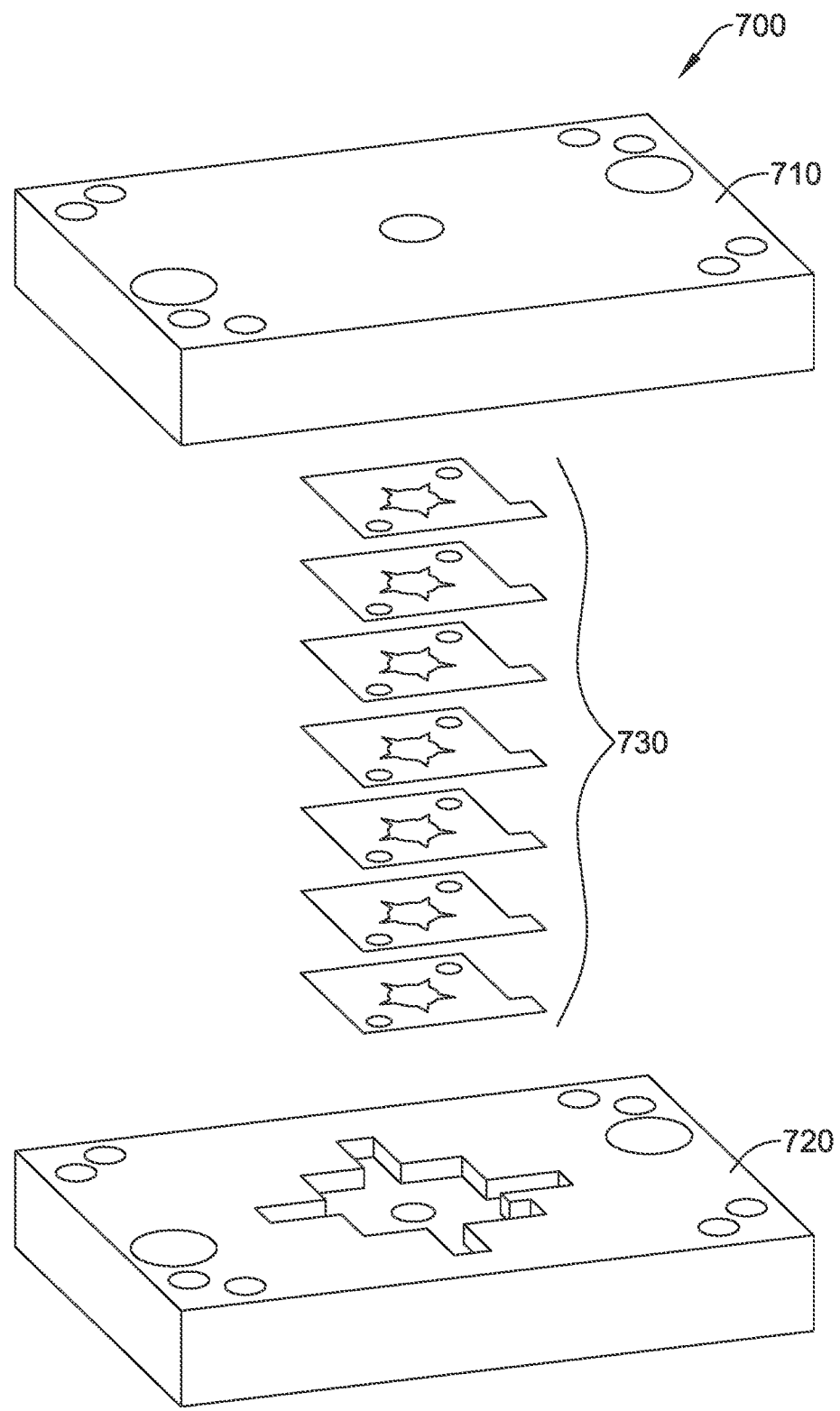
FIG. 17 is a perspective view of a mold prior to assembly, according to an embodiment of the present disclosure.

The inside out seal member 300 with projections 320 in any orientation may be manufactured by an injection molding process. In one example, the seal member 300 may be formed using a radially ejectable mold 600 as shown in FIG. 16. The radially ejectable mold 600 may include a plurality of radially moveable segments and a core element 650. The desired projection number and orientation is formed in the mold segments, which are removed radially to unmold the seal member 300, as indicated by arrows 660. The size of the core element 650 determines the dimensions of the outer wall 310 of the seal member 300. In another example, the seal member may be formed using an axially staked mold 700 as shown in FIG. 17. The axially staked mold 700 may include a top 710 and a base 720 and a series of staked projection orientation plates 730, each plate 730 defining the shape and orientation of one layer of projections 320.

In various embodiments, a seal member 100, 200, 300 may comprise a soft material such as a plastic, foam, silicone, rubber, or elastomer that may be suitable for sealing about a medical device extending therethrough. The precise form and materials for a seal member 100, 200, 300 may vary. For example, a seal member 100, 200, 300 may include a pliable or formable material that may or may not be absorbent. In some embodiments, a seal member 100, 200, 300 may include those materials used for similar structures disclosed in U.S. Pat. No. 6,663,598, filed May 17, 2000 and titled "Fluid Seal For Endoscope," the disclosure of which is herein incorporated by reference in its entirety and for all purposes. In at least some embodiments, a seal member 100, 200, 300 may extend laterally to the edges (and/or the top) of a shell 136, thereby substantially filling an inner chamber 132. This may help to prevent or reduce the amount of fluids that may migrate into and out from cap 130. Alternatively, a gap may be formed between the top of seal member 100, 200, 300 and the top of the inner chamber 132 of shell 136 and may be used, for example, to hold bodily fluids that may escape from seal member 100, 200, 300 and that may otherwise "splash" during, for example, device removal or exchange. In still further embodiments, a portion of seal member 100, 200, 300 may extend out from shell 136 and it may define or otherwise function as a strain relief.

In addition to being disposed in a biopsy cap 130 of an endoscope, the seal member 100, 200, 300 may also be applied to other similar applications as well where leakage prevention is required along device(s) inserted through the seal member 100, 200, 300. Additionally, having a downwards oriented flaps, the seal member 200 may also act as a one-way valve for sealing fluid inside the seal member 200.

The various biopsy caps, seal members, and molds as well as the various components thereof may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In addition, portions or components of the structures (including the various securing members, locking members, etc.) disclosed herein may be coated with a relatively soft material that may improve grip such as a thermoplastic elastomer. The coating may or may not include additional features that may improve grip such as ridges, surface textures, bumps, grooves, projections, etc.

Furthermore, the various structures disclosed herein may be designed for single use or may be designed for repeated uses. Thus, the structures disclosed herein may be manufactured from materials that can withstand multiple sterilizations and/or cleanings. This may be true of entire caps, as disclosed herein, or any of the various features of any of the caps.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The disclosure's scope is, of course, defined in the language in which the appended claims are expressed.

What is claimed is:

1. A seal for use in combination with an endoscope, the seal comprising:
    a main body including a circumferential outer wall surrounding a central lumen, the main body having a top surface and a bottom surface;
    at least one support wall extending radially from the outer wall towards a center of the lumen; and
    at least one helical flap extending from the support wall helically downward along an inner surface of the outer wall, wherein the at least one helical flap defines an opening at the center of the lumen;
    wherein:
    the at least one support wall consists of only first and second support walls; and
    the at least one helical flap consists of only first and second helical flaps.

2. The seal of claim 1, wherein the only first and second helical flaps each extend downward in a first direction helically along the inner surface of the outer wall and in a second direction radially towards the center of the lumen.

3. The seal of claim 1, wherein the at least one first helical flap extends from a top surface of the first support wall to a bottom surface of a second support wall.

4. The seal of claim 1, wherein each helical flap has a first end adjacent the top surface of the main body and a second end that extends below the bottom surface of the main body.

5. The seal of claim 1, wherein the opening is defined in part as a space between the first and second support walls, the space having a first diameter adjacent the top surfaces of the first and second support walls and a second diameter adjacent the bottom surfaces of the first and second support walls.

6. The seal of claim 1, wherein the first and second support walls are disposed directly opposite each other.

7. A seal for use in combination with an endoscope, the seal comprising:
- a main body including a circumferential outer wall surrounding a central lumen, the main body having a top surface and a bottom surface;
- at least one support wall extending axially along an inner surface of the outer wall and radially inwardly from the outer wall towards a center of the lumen; and
- only two helical flaps extending radially-inwardly from the inner surface of the outer wall, at least one of the helical flaps extending radially-inwardly from the axially-extending support wall and helically downward from the top surface of the main body toward the bottom surface of the main body along an inner surface of the outer wall.

8. The seal of claim 7, wherein each of the only two helical flaps extends radially inwardly toward the lumen and allows an instrument to pass axially through the seal.

9. The seal of claim 8, wherein the only two helical flaps define an axial opening therebetween allowing an instrument to pass axially through the seal.

10. The seal of claim 7, wherein each of the only two helical flaps has a first end adjacent the top surface of the main body and a second end that extends below the bottom surface of the main body.

11. The seal of claim 7, wherein the at least one support wall comprises two support walls disposed directly opposite each other, with a helical flap extending from each support wall.

12. The seal of claim 11, wherein each of the only two helical flaps defines substantially half of the seal.

13. The seal of claim 7, wherein the only two helical flaps each define substantially half of the seal.

14. The seal of claim 13, wherein the only two helical flaps extend radially inwardly towards the center of the lumen and allow an instrument to pass axially through the seal.

15. The seal of claim 7, wherein the at least one helical flap has a first end adjacent the top surface of the main body and a second end that extends below the bottom surface of the main body.

16. The seal of claim 7, wherein the at least one support wall comprises only two support walls, each with a helical flap extending radially-inwardly therefrom.

17. A biopsy cap comprising:
- an outer shell defining a cavity therein; and
- a seal disposed within the cavity of the outer shell;
- wherein the seal comprises:
  - a main body including a circumferential outer wall surrounding a central lumen, the main body having a top surface and a bottom surface;
  - a first support wall and a second support wall each extending radially from the outer wall towards a center of the lumen, the seal support walls comprising only the first and second support walls;
  - a first helical flap extending radially inwardly from the first support wall and helically downward along an inner surface of the outer wall; and
  - a second helical flap extending radially inwardly from the second support wall and helically downward along the inner surface of the outer wall.

18. The biopsy cap of claim 17, further comprising a base with a securing member for securing the biopsy cap to a port on the endoscope.

19. The biopsy cap of claim 17, further comprising a locking member.

20. The biopsy cap of claim 17, wherein the first and second helical flaps extend radially inwardly toward central lumen and allow an instrument to pass axially through the seal.

* * * * *